(12) United States Patent
Schmitz

(10) Patent No.: US 6,248,195 B1
(45) Date of Patent: Jun. 19, 2001

(54) THERMAL JOINING OF WEBS

(75) Inventor: Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/308,571

(22) PCT Filed: Nov. 18, 1997

(86) PCT No.: PCT/US97/21135

§ 371 Date: May 21, 1999

§ 102(e) Date: May 21, 1999

(87) PCT Pub. No.: WO98/22285

PCT Pub. Date: May 28, 1998

(30) Foreign Application Priority Data

Nov. 21, 1996 (EP) .................................................. 96118654

(51) Int. Cl.[7] ...................................................... B32B 31/26
(52) U.S. Cl. .................... 156/82; 156/290; 156/308.4; 604/358
(58) Field of Search .......................... 156/82, 290, 308.2, 156/308.4, 324; 604/358, 378, 379, 380

(56) References Cited

U.S. PATENT DOCUMENTS

| | | | |
|---|---|---|---|
| 3,468,096 | 9/1969 | Franz | 53/28 |
| 3,617,417 | 11/1971 | Olson | 156/181 |
| 3,788,917 | 1/1974 | Linda | 156/82 |
| 4,099,943 | 7/1978 | Fischman et al. | 55/487 |
| 4,184,902 | 1/1980 | Karami | 156/85 |
| 4,311,745 | 1/1982 | Civardi | 428/91 |
| 4,610,681 | 9/1986 | Strohbeen et al. | 604/396 |
| 4,883,707 | 11/1989 | Newkirk | 428/219 |
| 4,919,738 | 4/1990 | Ball et al. | 156/73.5 |
| 5,360,420 | * 11/1994 | Cook et al. | 604/378 |

FOREIGN PATENT DOCUMENTS

| | | |
|---|---|---|
| 23 31 864 A1 | 1/1975 | (DE) . |
| 28 39 985 A1 | 3/1979 | (DE) . |
| 2024099 | 1/1980 | (GB) . |
| 57-140151 | 8/1982 | (JP) . |

OTHER PUBLICATIONS

European Search Report dated 25/4/97 for App. No. 96118654.1.

* cited by examiner

*Primary Examiner*—James Sells
(74) *Attorney, Agent, or Firm*—Michael S. Kolodesh; David M. Weirich; Ken K. Patel

(57) ABSTRACT

A method of joining at least two webs (11, 12), said webs (11, 12) being porous and comprising meltable components, said webs (11, 12) being arranged in an adjacent manner to form a web structure (10), said web structure (10) comprising outer surfaces (13, 14) and an area of overlap (15) between said webs (11, 12); said method characterized by the steps of: 1) sufficiently heating a fluid to enable at least a partial melting of said meltable components; 2) directing a high speed jet of said heated fluid towards at least one of said outer surfaces (13, 14); 3) allowing said fluid to penetrate said webs (11, 12) at discrete locations; and 4) allowing said fluid to circulate in said webs (11, 12) to at least partially melt said meltable components. In another aspect of the invention, a disposable absorbent article Is made according to the method described herein.

13 Claims, 1 Drawing Sheet

THERMAL JOINING OF WEBS

FIELD OF THE INVENTION

The present invention relates to a method for the thermal joining of webs. Its application is intended for use in disposable absorbent articles.

BACKGROUND OF THE INVENTION

Disposable absorbent articles, in particular, disposable diapers are well known articles of manufacture which are designed to be worn principally by infants and incontinence sufferers. Such diapers are worn about the lower torso of the wearer and are intended to absorb and contain urine and other bodily discharges, thus preventing the soiling, wetting, or similar contamination of articles (e.g., clothing, bedding, other persons, etc.) that may come into contact with such a diaper in use. In recent years, disposable diapers in the form of pull-on diapers have emerged on the market and in particular, disposable pull-on diapers with fixed sides have gained in popularity. Typically, the fixed sides of the disposable pull-on diaper are manufactured by joining the side panels of the front portion to the side panels of the rear portion. For joining purposes, the contacting surfaces of the side panels need to be at least partially melted. It is, however, desirable to avoid melting the outer surfaces of the side panels corresponding to the area to be joined. In general, a technique which permits the joining of several layers of thick material that does not lead to the formation of hard, raspy protuberances on the outer surfaces is required. It has been documented that current techniques are more easily suited to the joining of thin layers of material. Therefore, the problem of joining thick materials is known in the art but the only solutions proposed hitherto, as far as the present applicants are aware, are those described hereforth.

Typical of prior art processes are the conventional thermal joining processes, which utilise hot pins made of steel, aluminium and copper or other materials with a high coefficient of thermal conductivity to transfer the required energy for melting into the webs to be joined. For thin materials like films, the hot pins touch and melt the outer surfaces of the web structure. For thicker materials, it is preferred that the hot pins penetrate the whole web structure. The upward and downward action of the hot pins results in both the creation of holes with molten walls and some of the melted material being displaced and transported to the surface of the web structure to form—after cooling—hard, raspy protuberances. In order to ensure that an effective joining takes place, compression of the web structure subsequently follows. Nevertheless, before the compression tools can be placed in position, the hot pins have to be moved away resulting in a complex operation. It is only when the melted material has cooled that the compression tools are removed from the web structure.

The perforation of a film material generally, but not exclusively of, thermoplastic material is taught in U.S. Pat. No. 4,667,552. Heated perforation pins are carried by a rotating cylinder and the film to be perforated is forced against the pins by a pressure means such as a deformable roller. The hot pin enters from the top of the plastic film and as the hot pin melts the surrounding film after the pin perforates the film, the film is melted into an 'upset' structure. The film, after perforation, has one smooth face and an obverse face that has a texture due to the proliferation of protuberances. The technique is not suitable for the joining of thick materials.

U.S. Pat. No. 4,519,798 typifies a process that utilises thermal energy to soften two or more layers of thermoplastic material for the purposes of joining. The patent discloses a disposable diaper structure wherein an absorbent core is encapsulated between a multiplicity of sheets. Each of the sheets is constructed of a material, such as polyethylene, which will heat seal without the necessity of an adhesive. The diaper is made by heating and sealing the overlapping edges of the polyethylene sheets directly to one another outside the borders of the absorbent core.

The autogenous lamination of plural layers or laminae of sheet material are described in U.S. Pat. No. 4,919,738. In more detail, the patent teaches a method of dynamically bonding plural laminae together, at least one of which laminae comprises thermoplastic material. The lamination is achieved through the use of pressure biased laminating rolls which are operated with a predetermined surface velocity differential between them. Indeed, in some lamina, portions of the bonding sites may protrude resulting in hard, raspy protuberances rather than being recessed.

Layers of thermoplastic materials are welded together by means of ultrasonic vibration equipment in U.S. Pat. No. 3,733,238. A plurality of spaced ultrasonic vibration transmitting members having working surfaces in direct contact with one side of the sheet-like elements is employed in co-operation with opposing spaced anvil surfaces located on the opposite side of the sheet-like elements to produce full width webs of thermoplastic laminated material. As is evident, the technique requires that the layers of thermoplastic material are always in direct physical contact with the mechanical energy transfer tools, thus leading to contamination of the webs, machine wear and thus machine inefficiency.

A seam composed of a six-layered structure comprising the outer fabric layer, the inner impermeable layer of the cover sheet and the permeable layer forming the liner of the garment is disclosed in U.S. Pat. No. 4,610,681. In order to form a small and unobtrusive bond, the ultrasonic sealing is accomplished with a plurality of lines that form pressured areas and raised line areas. As above, the technique is mechanical in nature and results in contamination of the webs, machine wear and machine inefficiency.

A means of joining thick layers of material is outlined in U.S. Pat. No. 4,909,804, which discloses seams of a disposable training pant that have been joined by stitching.

WO 96/19313 describes a method for forming through apertures in the form of holes and/or slits in a web that is intended to form part of an absorbent article, e.g., the topsheet of an absorbent article being apertured to obtain liquid permeability. According to the invention, a web is irradiated with at least one focused electromagnetic beam or particle beam from an irradiating source on at least one of its surfaces and in those web regions where the apertures are to be formed. During irradiation the web can be in contact with another web which includes material of a kind similar to the first web and the properties of the beam and the duration of the irradiation period are chosen so that the material in the first web and/or in the further web will be supplied with sufficient energy to join the webs in the immediate vicinity of the apertures. A fluid may be delivered to the vicinity of the focusing point on the web to remove molten/burned/vaporised material from holes made in the web. In spite of the lack of contact with the webs to be joined, the technique focuses on aperturing and results in melted material being displaced and transferred to the topsheet surface.

Needlepunching is a mechanical bonding technique which is utilised to join webs of material. In U.S. Pat. No.

5,397,632, non-woven webs for use in an improved automotive depth air filter are mechanically secured at intermittent locations. During the needlepunching operation, a plurality of needles having a fibre advancing configuration are passed through all the webs. The various webs thus become mechanically interconnected and interlocked through the entanglement of staple fibres and filaments. During such needle insertion and withdrawal, staple fibres from the upper web and relatively mobile fibres from the intermediate web are driven forward and into the lower web. The surface of the final product is not smooth to the touch.

As a result of the above prior art attempts, it has been recognised by those skilled in the art that it would be desirable to provide a method of joining thick webs for particular use in disposable absorbent articles that eliminates the presence of hard, raspy protuberances on the outer surfaces caused by the solidification of melted web material; that does not require the use of heat transfer tools that come into physical contact with the webs to be joined; that at least partially melts the meltable components in the web structure to render a sufficient tackiness for joining; and that results in a product with superior tactile properties and concomitant strength, resistance to wear and breathability characteristics. The solution was found to be a method wherein a high speed jet of heated fluid is directed into the outer surface of at least two thick and porous webs at discrete locations and wherein the constituent meltable components are at least partially melted in the area of overlap of the web structure.

It has now been discovered that the benefits of the present invention range from a method that enables the joining of thick, porous webs in an extremely effective manner; to a method that eliminates the irritating hard and raspy protuberances of the prior art techniques; to a method that does not rely on heat transfer tools coming in contact with and contaminating the web structure as is typical of conventional joining processes; to a method that minimises process time; to a method that leads to improved machine efficiency due to reduced wear and friction; and to a product with enhanced tactile qualities and superior resistance to wear characteristics leading to improved consumer satisfaction and confidence.

SUMMARY OF THE INVENTION

A method of joining at least two webs is described. The webs are porous, comprise meltable components and are arranged in an adjacent manner to form a web structure. The web structure comprises outer surfaces and an area of overlap joining the webs. The method is characterised by the steps of:

1) sufficiently heating a fluid to enable at least a partial melting of the meltable components;
2) directing a high speed jet of the heated fluid towards at least one outer surface of the webs;
3) allowing the fluid to penetrate the webs at discrete locations; and
4) allowing the fluid to circulate in the webs to at least partially melt the meltable components.

The method further comprises the step of compressing and cooling the web structure while the meltable components are at least partially melted.

In particular, the method is used in the manufacture of disposable absorbent articles. In a preferred embodiment of the invention, the method is used to make the side seams of a pull-on diaper.

In a further aspect of the invention, a disposable absorbent article is made according to the method described herein.

The preferred embodiment of this aspect of the invention describes a pull-on diaper with the webs comprising the side panel of the front portion and side panel of the rear portion, which are joined to form overlapping side seams, i.e., the web structure.

BRIEF DESCRIPTION OF THE DRAWINGS

It is believed that the invention will be better understood from the foregoing description in conjunction with the accompanying drawings in which.

DETAILED DESCRIPTION OF THE INVENTION

As used herein, the term "joining" encompasses the configuration whereby an element is directly secured to another element by affixing the element directly to the other element. As meant herein, the term "web" refers to a layer of material(s). The term "layer" does not necessarily limit the web to a single stratum of material. As used herein, the term "disposable" describes absorbent articles that are not intended to be laundered or otherwise restored or reused as an absorbent article (i.e., they are intended to be discarded after a single use and, preferably, to be recycled, composted or otherwise disposed of in an environmentally compatible manner. The term "pull-on diaper" refers to a garment that is generally worn by infants and sufferers of incontinence, which is pulled on like pants, and which is intended to be discarded after a single use. It should be understood, however, that the present invention is also applicable to other pull-on diapers such as training pants, incontinence briefs, feminine hygiene garments or panties, and the like.

Figure 1:
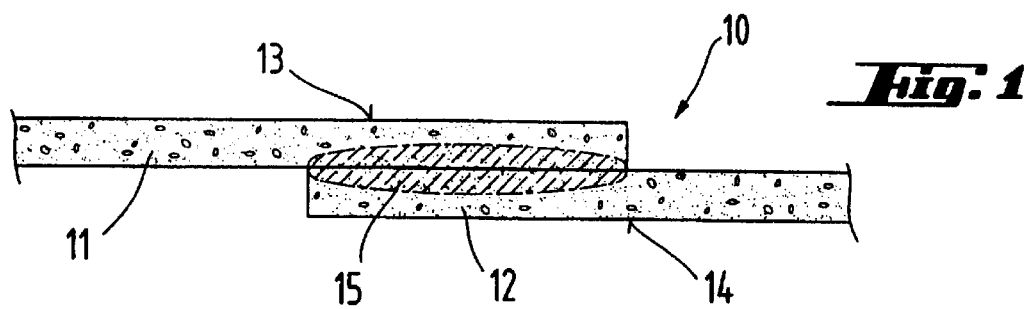
FIG. 1 schematically illustrates a fragmentary side elevational view of the webs.

A somewhat schematic, fragmentary side elevational view of the webs to be joined is shown in FIG. 1. In particular, FIG. 1 shows at least two porous webs 11, 12 that have been arranged in an adjacent manner to form a web structure 10. The web structure 10 comprises outer surfaces 13, 14 and an area of overlap 15 between the webs 11, 12.

The joining of webs is possible according to the teachings of the present invention provided that at least one of the webs comprises sufficient meltable material that is susceptible to being thermally joined to another web. The present invention teaches webs that are porous—air permeable, fluid permeable or vapour permeable—and that comprise meltable components. The web can either be woven or nonwoven and the meltable components may comprise fibres or polymeric binders and can include natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; and binders such as bicomponent high melt/low melt polymer, copolymer polyester, polyvinyl chloride, polyvinyl acetate/chloride copolymer, copolymer polyamide. The webs may additionally comprise blends of materials wherein some of the constituent materials are not meltable.

Figure 2:
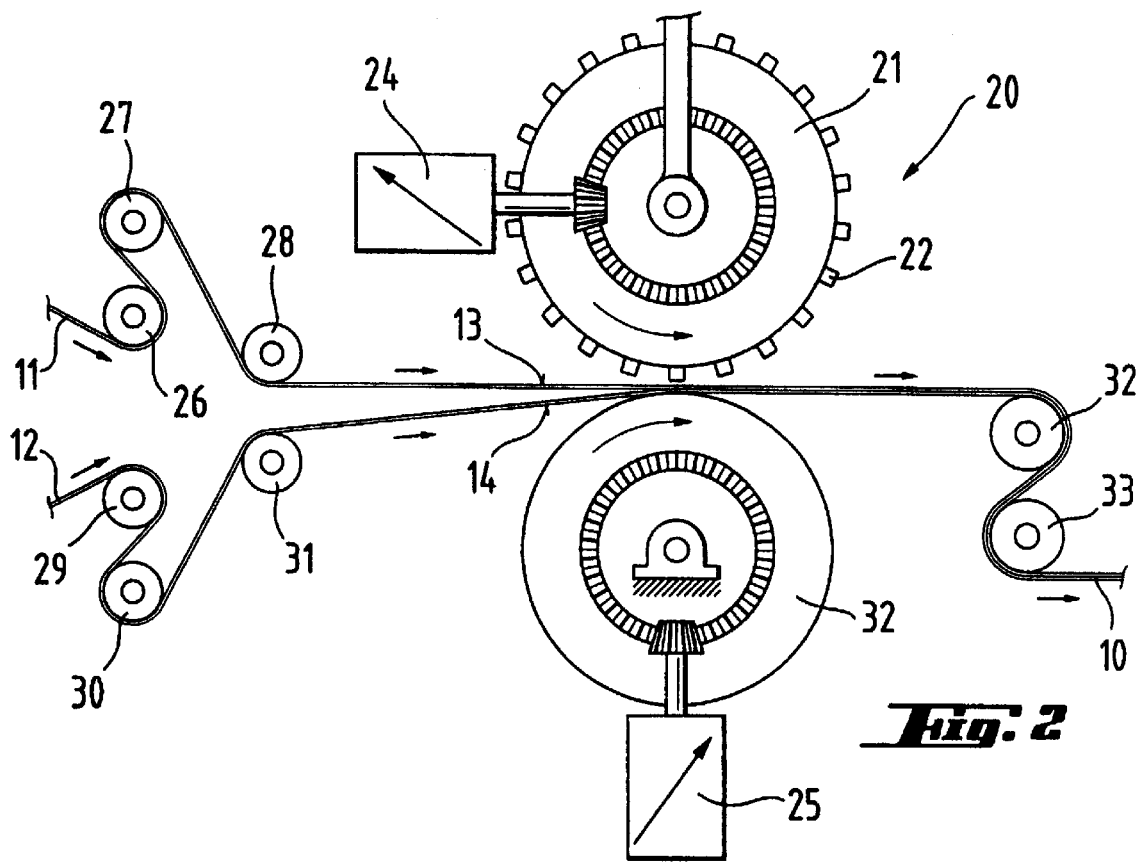
FIG. 2 shows a simplified schematic drawing of the apparatus used for joining webs.

FIG. 2 shows a simplified schematic drawing of the apparatus used for joining webs 11, 12 to form a web structure 10 in accordance with the method of the present invention. The apparatus 20 comprises a cylinder 21 with projections 22; an anvil cylinder 23; a means 24, 25 for rotating the cylinders 21, 23; and rolls 26 to 33, inclusive, for guiding and advancing the webs 11, 12 through and away from the point at which energy transfer occurs. It should be noted that there is no need to heat the cylinder 21 and anvil cylinder 23. The apparatus 20 additionally comprises a frame (not shown); a fluid jet nozzle leading to the projections 22 (not shown); a temperature control means (not shown) for heating up the fluid; a pressure means (not shown) for regulating the pressure of the fluid; and means (not shown) for driving the rolls 26 to 33 for controllably forwarding webs 11, 12 through the point at which the energy transfer occurs and for enabling the resulting web structure 10 to be forwarded to downstream apparatus such as a single pad handling apparatus, which tucks in the fixed sides of the diapers.

For clarity of the present invention, neither the upstream ends or sources of webs 11, 12, nor the downstream destination or user of the web structure 10 are shown. Nevertheless, it is well known to provide webs in roll form; and to provide upstream unwinding and splicing means to enable forwarding continuous lengths of such webs through joining means and or converters to make web structures. For simplicity of the present invention, the apparatus 20 is described herein as comprising a cylinder 21 and an anvil cylinder 23. It is not intended in any way to limit the invention to an apparatus comprising cylinders per se.

Figure 3:
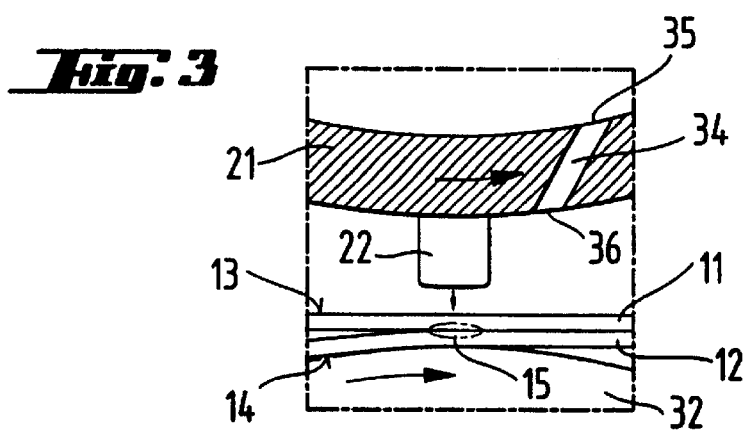
FIG. 3 illustrates a simplified and partially sectioned view of a cylinder with a representative projection.

FIG. 3 shows a simplified and partially sectioned view of the cylinder 21 with a representative projection 22. The cylinder 21 comprises either a conical or cylindrical shaped zone 34 through which the fluid required to at least partially melt the meltable components of the webs 11, 12 is directed. In FIG. 2, for simplicity, a cylindrical shaped zone 34 is drawn. A fluid jet nozzle (not shown) is connected to the top face 35 of a conical or cylindrical shaped zone 34. The fluid is preferably air although other gases may be used. In addition, use can be made of energetic fields to achieve the same partial melting effect. In the present invention, the fluid is heated up to a temperature ranging from the melting point of the material minus 30 degrees celsius to the melting point of the material plus 100 degrees celsius. The pressure ranges from 0.1E5 Newtons per square meter to 10E5 Newtons per square meter. The diameter at the top face 35 of the conical or cylindrical shaped zone 34 ranges from 1 millimeter to 8 millimeters and the diameter of the orifice 36 of the conical or cylindrical shaped zone 34 ranges from 0.1 millimeters to 6 millimeters. The conical or cylindrical shaped zone 34 moves preferably with the same or almost same speed as the area of overlap 15 of the webs 11, 12 for an extended time interval ranging from 10 to 1000 milliseconds. This enables the heated fluid to be directed towards at least one outer surface 13, 14, as required, to achieve optimum quality seams in terms of strength and softness. The projections 22 on the cylinder 21 may be disposed in a predetermined pattern: each projection being configured and disposed to precipitate areas of overlap 15 in the webs 11, 12 to be joined to effect a predetermined pattern of areas of overlap 15 in the web structure 10. The cylinder 21 may have a saw-tooth shape pattern of projections 22 which extend circumferentially about each end of the cylinder 21.

The anvil cylinder 23 is preferably a smooth, surfaced, right circular cylinder of steel, which can be independently power rotated by a speed controlled direct current motor. In an alternative configuration, the anvil cylinder 23 moves preferably with the same speed as the webs 11, 12 at the area of overlap 15 for an extended period of time ranging from 20 to 1000 milliseconds. During this time interval, the area of overlap 15 is deformed, joining occurs and cooling follows. There may also be a number of anvils and fluid jet nozzles mounted on a carrier at a pitch ranging between 0.5 and 1.5 times the product pitch.

The means 24, 25 are provided to drive the cylinder 21 and anvil cylinder 23. Therefore, they constitute drive means for power rotating the cylinder 21 and anvil cylinder 23 so that there is a predetermined but adjustable relationship between their surface velocities. This can be synchronous, asynchronous: equal surface velocities; or with a predetermined surface velocity differential with either cylinder 21 or anvil cylinder 23 being driven faster than the other. The rolls 26 to 33, inclusive, are driven at surface velocities which maintain predetermined levels of tension or stretch so that neither slack web conditions nor excessively tensioned/stretched webs precipitate undesirable deleterious consequences.

According to the inventive method of the present invention, the joining of at least two webs 11, 12 that are arranged in an adjacent manner to form a web structure 10 as illustrated in FIG. 1 comprises the following steps of: sufficiently heating a fluid to enable at least a partial melting of the meltable components; directing a high speed jet of the heated fluid towards at least one outer surface 13, 14; allowing the fluid to penetrate the webs 11, 12 at discrete locations; and allowing the fluid to circulate in the webs 11, 12 to at least partially melt the meltable components. The heated fluid, at a preferred temperature and pressure, passes from the fluid jet nozzle into the conical or cylindrical shaped zone 34 of the projection 22 and out through the orifice 36, leading to the formation of controlled and concentrated jets of heated fluid, which are directed towards the outer surfaces 13, 14 of the webs 11, 12 to be joined. The fluid can also be delivered to the outer surfaces 13, 14 by means of a pulsed application. The impact of the jet of heated fluid is adjusted such that both the energy introduced by the jet per se plus the energy introduced by other means such as the heated anvil (if this is the case), jet nozzle surface, deformation of the webs 11, 12, and the internal friction of the webs 11, 12 are sufficient to at least partially melt the meltable components in the webs 11, 12 to create a certain tackiness, which will form a strong join at the area of overlap 15 upon compression. The melting of the meltable components occurs in a non-uniform manner throughout the webs 11, 12. In particular, the exterior surface of the meltable components begins to melt leaving the interior of the meltable components in the solid state. As a consequence of the exterior melting of the meltable components, a certain tackiness is created.

The method further comprises the step of compressing the web structure 10 with compression tools while the meltable components are at least partially melted, i.e., in the tacky state. This is achieved by applying pressure to the web structure 10 using compression tools. The temperature of the compression tools is at least below the melting point of the web structure 10. The tackiness property of the meltable components permits the joining of the webs 11, 12 and thus, the accumulation of melted web material is avoided. Such melted material typically forms the hard, raspy protuberances on the outer surfaces of so many web structures upon solidification. The compression tooling can be, designed according to aesthetic criteria.

Good results are obtained with this method on non-woven webs ranging from 30 to 500 grams per square meter containing fibres ranging from microfibres of less than one denier to conventional fibres ranging from 1 to 7 denier. The non-woven webs may also contain scrim materials having strands with diameters greater than 1 millimeter. Due to the thickness of the webs, the interval of time required to affect the webs 11, 12 with this technique ranges from 100 to 1000 milliseconds. In this particular application, 100 to 150 milliseconds is required for heating and 150 to 250 milliseconds is required for compression/cooling.

In a further aspect of the present invention, the method as described hereinabove is used in the manufacture of disposable absorbent articles. In particular, the method is preferably used in the making of side seams for disposable absorbent articles wherein the disposable absorbent articles are disposable pull-on diapers. A disposable pull-on diaper, made according to the method of the present invention, has an outer surface, an inner surface, a front portion, a rear portion, a crotch portion, each of said front portion and said rear portion having side panels with side edges and overlapping side seams which join together the side panels of the front portion and the rear portion to form leg openings and a waist area. The pull-on diaper thus preferably comprises a chassis layer; an elastically extensible stretch laminate positioned in each side panel of the front portion, front stretch laminates; an elastically extensible stretch laminate positioned in each side panel of the rear portion, rear stretch laminates; and at least one elasticised waistband positioned in both the front portion and the rear portion. The pull-on diaper comprise leg openings which additionally comprise elastic leg features to improve fit at the legs in the crotch portion.

The pull-on diaper has a crotch portion comprising a main panel and a pair of leg flap panels. The absorbent core is generally positioned within the main panel of the crotch portion since bodily exudates are typically discharged in this area. A leg flap panel extends generally laterally outwardly from and along each side edge of the main panel. Each leg flap panel generally forms at least a portion of the elastic leg feature. The outer surface of the pull-on diaper comprises that portion which is positioned away from the body of the wearer during use. The inner surface of the diaper is opposed to the outer surface and comprises that portion of the diaper which is positioned adjacent to the body of the wearer during use.

Elastically extensible stretch laminates (front stretch laminates and rear stretch laminates) are formed in each side panel of both the front portion and the rear portion. Each stretch laminate is mechanically stretched or drawn to allow the stretch laminate to be elastically extensible in at least the lateral direction. (The lateral direction (x direction or width) is defined as the direction parallel to the lateral centreline of the pull-on diaper. The side panels are preferably an extension of the chassis layer and other elements such as the topsheet, or any other combination of these elements. In the overlapping side seams, the stretch laminate is preferably activated by mechanical stretching to provide additional extensibility in this region. The overlapping side seams may also not be activated by mechanical stretching.

In order to provide the necessary absorbency to contain bodily discharges, the pull-on diaper comprises a liquid pervious topsheet and an absorbent core positioned between the topsheet and the chassis layer. The topsheet is positioned adjacent to the body surface of the absorbent core and is preferably joined to the absorbent core and the chassis layer by attachment means such as those well known in the art. In a preferred embodiment, the topsheet and the chassis layer are indirectly joined together by directly joining them to the absorbent core or the elastic panel members or other elements of the pull-on diaper. The topsheet preferably comprises three distinct layers joined together. A liquid pervious primary layer is positioned over the absorbent core to rapidly absorb liquids into the product. Barrier layers are joined to the primary layer and are preferably drawable, more preferably hydrophobic, to allow the side panels to be mechanically stretched without ripping or tearing while providing barrier cuffs along the sides of the pull-on diaper. The elastic leg features preferably comprise a gasketing cuff and a barrier cuff. The gasketing cuff is preferably formed by one or more elastic leg members operatively joined to the chassis layer, the barrier layer, or both, preferably between the chassis layer and the flap portion of the barrier layer in the leg flap panel of the crotch portion. The barrier cuff is preferably formed by a flap (the stand-up portion of the barrier layer, closing means for securing the longitudinal ends of the stand-up portion to the primary layer, and an elastic spacing member operatively joined to the stand-up portion.

The primary layer is preferably compliant, soft feeling, and non-irritating to the skin of the wearer. The primary layer is liquid pervious permitting liquids (e.g., urine) to readily penetrate through its thickness. A suitable primary layer may be manufactured from a wide range of materials, such as porous foams; reticulated foams; apertured plastic films or three dimensionally expanded formed films; or woven or nonwoven webs of natural fibers, synthetic fibers, or a combination of natural and synthetic fibers. The primary layer is preferably non-coterminous with the chassis layer so that liquid will not wick along and through the primary layer to the edges of the pull-on diaper, so that liquids will not wick underneath and beyond the stand-up barrier cuffs formed by the barrier layers, and so that more drawable materials may be positioned in the side panels to produce stronger stretch laminates. The primary layer preferably overlays a major portion of the body surface of the absorbent core, more preferably all of the body surface area of the absorbent core in at least the crotch portion, so that exudates that are discharged into the pull-on diaper penetrate through the primary layer where they are absorbed by the absorbent core. The primary layer extends laterally outwardly toward the side edges of the absorbent core, preferably beyond the side edges of the absorbent core in at least the crotch portion. The primary layer, however, terminates inwardly of the leg edges of the crotch portion. In the most preferred configurations, the primary layer terminates adjacent the proximal edge of the barrier layer (i.e., the terminating edge of the primary layer is positioned adjacent to the proximal edge) or the terminating edge is positioned remotely from and inboard of the proximal edge. "Adjacent" is used in this context to mean that the primary layer terminates at the proximal edge plus or minus small areas of the primary layer material that may extend inside or beyond the proximal edge due to machine tolerances during manufacture or variations in the area of the primary layer when it is manufactured. In the preferred embodiment of the topsheet, the barrier layers form the elastic leg features (preferably, a gasketing cuff and/or a barrier cuff) and, preferably, a portion of the stretch laminates.

The chassis layer preferably comprises a continuous sheet or web which defines the front portion, the rear portion, and the crotch portion. Thus, the chassis layer is the primary stratum or layer of the pull-on diaper. (As used herein, the term "layer" does not necessarily limit the element to a single stratum of material in that a layer may actually comprise laminates or combinations of sheets or webs of the requisite type of materials.) The chassis layer has an inner surface and an outer surface. The inner surface and outer surface of the chassis layer correspond in their orientation to the inner surface and the outer surface of the pull-on diaper.

The chassis layer generally determines the overall shape of the pull-on diaper. The chassis layer acts as the main structural layer of the pull-on diaper to which other features may be added or joined. The chassis layer is thus positioned in all or most of the surface area of the pull-on diaper, although in certain embodiments certain portions of the chassis layer may be apertured, cut-out or removed ("windowed") to enhance stretchability and/or breathability of the pull-on diaper or features of the pull-on diaper in that area. The chassis layer thus may comprise a continuous sheet or web that does not have "joints" or seams such that forces are distributively transmitted through the entire layer or the chassis layer may comprise a continuous sheet or web that does have "joints" with the elasticised leg cuffs. As previously discussed herein, the continuous sheet or web of the chassis layer can comprise a single web of material or a laminate of several continuous webs or layers of different materials. The chassis layer may form the outer surface, the inner surface, or portions of either or both, or may be entirely positioned in the interior of the pull-on diaper. The chassis layer preferably forms the outer surface of the pull-on diaper in the crotch portion.

Since at least a portion of the chassis layer is subjected to mechanical stretching in order to provide the stretch laminates in the side panels, it is preferably elongatable, more preferably drawable (but not necessarily elastomeric), so that the chassis layer will, upon mechanical stretching, be at least to a degree permanently elongated such that it will not fully return to its original undistorted configuration. The chassis layer may thus comprise any of the materials known for use in absorbent articles such as woven or nonwoven webs; polymeric films such as thermoplastic films of polyethylene, polypropylene, or blends thereof; laminates of such materials; or composite materials. In preferred embodiments, the chassis layer can be subjected to mechanical stretching with minimal or no rupturing or tearing. Therefore, the chassis layer is preferably a polymeric film.

Due to the fact that the chassis layer is preferably a polymeric film, it is also generally impervious to liquids (e.g., urine) so that it may also serve as the component which prevents bodily discharges absorbed and contained in the absorbent core from wetting garments which contact the pull-on diaper 10 such as bed sheets and undergarments (i.e., it acts as the traditional diaper backsheet). If the chassis layer is not liquid impervious, typically an additional layer such as a traditional backsheet should be used behind the absorbent core. The chassis layer may also be breathable (pervious to air or water vapour) if desired. The chassis layer can alternatively comprise breathable materials that are microporous and that are, typically, lower in strength and elongation. An example of such a film is that manufactured by Exxon Chemical Company under the tradename EXXAIRE. Exemplary films for use as the chassis layer of the present invention having relatively good drawability but that are not breathable include polymeric films manufactured by Clopay Corporation of Cincinnati, Ohio under the designation Clopay 1401, or films available from Tredegar of Terre Haute, Ind., under the designation X-8323 or X-9954.

The pull-on diaper comprises a leg area that comprises elasticised leg cuffs for providing improved containment of liquids and other bodily exudates. The elastic leg features provide improved containment of liquids and other body exudates in the crotch portion and about the leg openings in general. Each elastic leg feature may comprise several different embodiments for reducing the leakage of body exudates in the leg flap panels (the elastic leg feature can be and is sometimes also referred to as leg bands, side flaps, barrier cuffs, or elastic cuffs.) U.S. Pat. No. 3,860,003 describes a disposable diaper which provides a contractible leg opening 16 having a side flap and one or more elastic panel members to provide an elasticized leg cuff (gasketing cuff). U.S. Pat. No. 4,909,803 discloses a disposable diaper having "stand-up" elasticized flaps (barrier cuffs) to improve the containment of the leg regions. U.S. Pat. No. 4,695,278 teaches a disposable diaper having dual cuffs including a gasketing cuff and a barrier cuff. U.S. Pat. No. 4,795,454 discloses a disposable diaper having leakage resistant dual cuffs wherein the topsheet stops short of the side edge of the diaper to prevent wicking out to the side of the garment. While each elastic leg feature may be configured so as to be similar to any of the leg bands, side flaps, barrier cuffs or elastic cuffs described above, it is preferred that each elastic leg feature comprise a combination of a gasketing cuff and a barrier cuff. The gasketing cuff and barrier cuffs are preferably formed as shown in U.S. Pat. No. 4,795,454.

The absorbent core is preferably positioned adjacent to the inner surface of the chassis layer and is preferably joined thereto by attachment means such as those well known in the art. For example, the chassis layer may be secured to the absorbent core by a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art. It may also be possible to apply the method of the present invention to join the chassis layer to the absorbent core.

The absorbent core may be any absorbent means which is generally compressible, conformable, non-irritating to the skin of the wearer, and capable of absorbing and retaining liquids such as urine and other certain bodily discharges. The absorbent core may be manufactured in a variety of sizes and shapes (e.g., rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core may also be varied (e.g., the absorbent core may have varying caliper zones, hydrophilic gradients, superabsorbent gradients, or lower average density and lower average basis weight acquisition zones; or may comprise one or more layers or structures). The total absorbent capacity of the absorbent core should, however, be compatible with the design loading and the intended use of the pull-on diaper. Further, the size and absorbent capacity of the absorbent core may be varied to accommodate wearers ranging from infants through adults.

In general, the absorbent core has an asymmetric, modified hourglass shape and has a body surface toward the body of the wearer (inner surface) and a garment surface opposite the body surface. An exemplary absorbent structure for use as the absorbent core of the present invention that has achieved wide acceptance and commercial success is described in U.S. Pat. No. 5,360,420. Preferably, the absorbent core will comprise an acquisition/distribution layer of chemically stiffened cellulosic fibers and a storage layer positioned beneath the acquisition/distribution layer comprising a mixture of wood pulp fibers and superabsorbent material such as are disclosed in U.S. Pat. No. 4,610,478.

The pull-on diaper can also be preferably provided with vents or apertures to permit the passage of air and water vapour to and from the interior of the pull-on diaper. In a preferred embodiment, the apertures are positioned in the side panels. In this configuration, bodily discharges are prevented from leaking out of the areas adjacent to the absorbent core but air and water vapour are allowed to be exchanged in the product to ventilate it so that the product does not become excessively wetted by body perspiration and uncomfortable to wear. Vents may additionally be provided in other panels of the pull-on diaper or on certain of the features of the pull-on diaper such as the waistband. Breathability may alternatively be provided by making the materials of the pull-on diaper out of porous materials such as are known in the art. For example, the chassis layer could comprise a breathable (vapour permeable) but liquid impervious plastic film. The elastic panel members may be open material such as foams, scrims, nonwovens, or breathable elastomeric films to further enhance the breathability of the pull-on diaper. The overlapping side seams retain good breathability properties if manufactured according to the method of the present invention. The waistband can also be breathable to allow water vapour to escape from the front portion and the rear portion of the pull-on diaper. Breathability may be provided in the waistband by selecting relative breathable materials for its construction and/or by aperturing or venting the waistband such as is discussed herein with respect to the stretch laminates in the side panels. In another embodiment, the waistband may be hydrophobic, hydrophilic, or a combination hydrophobic/hydrophilic member. A hydrophilic waistband may be used to pull moisture away from the skin of the wearer to keep the skin from becoming hydrated. Alternatively, a hydrophobic waistband may be used to prevent fluid absorbed by the diaper from leaking out through the waist opening. A combination hydrophobic/hydrophilic waistband may be used to prevent fluid absorbed by the diaper from leaking out through the waist opening while also pulling moisture away from the skin of the wearer to keep the skin from becoming hydrated.

In general, seams for disposable pull-on diapers can be formed by joining the side panels of the front portion to the side panels of the rear portion. According to a preferred embodiment of the present invention, the disposable pull-on diaper comprises the side panel of the front portion and the side panel of the rear portion. The side panels are joined to form overlapping side seams, i.e., a web structure 10, according to the method outlined herein.

What is claimed is:

1. A method of joining at least two webs, said webs being porous and comprising meltable components, said webs being arranged in an adjacent manner to form a web structure, said web structure comprising outer surfaces and an area of overlap between said webs; said method comprising the steps of:
   1) sufficiently heating a fluid to enable at least a partial melting of said meltable components;
   2) directing a high speed jet of said heated fluid towards at least one of said outer surfaces;
   3) allowing said fluid to penetrate said webs at discrete locations; and
   4) allowing said fluid to circulate in said webs to at least partially melt said meltable components.

2. A method according to claim 1 further comprising the step of compressing said web structure with compression tools while said meltable components are at least partially melted.

3. A method according to claim 2 wherein temperature of said compression tools is at least below melting point of said web structure.

4. A method according to claim 1 wherein at least said partial melting of said meltable components is primarily in said area of overlap.

5. A method according to claim 1 wherein at least said partial melting of said meltable components occurs in a non-uniform manner throughout said webs.

6. A method according to claim 1 wherein said fluid is air.

7. A method according to claim 1 used in the manufacture of disposable absorbent articles.

8. A method according to claim 4 used in the manufacture of disposable absorbent articles.

9. A method according to claim 7 used in the making of side seams wherein said disposable absorbent article is a disposable pull-on diaper.

10. A disposable absorbent article made according to the method of claim 1.

11. A disposable absorbent article made according to the method of claim 4.

12. A disposable absorbent article according to claim 10 wherein said disposable absorbent article is a disposable pull-on diaper and said web structure comprises the side panel of the front portion and side panel of the rear portion joined to form overlapping side seams.

13. A disposable absorbent article according to claim 11 wherein said disposable absorbent article is a disposable pull-on diaper and said web structure comprises the side panel of the front portion and side panel of the rear portion joined to form overlapping side seams.

* * * * *